United States Patent
Van Der Linde et al.

(10) Patent No.: US 12,102,412 B2
(45) Date of Patent: Oct. 1, 2024

(54) GUIDEWIRE FOR OPTICAL SHAPE SENSING

(71) Applicant: KONINKLIJKE PHILIPS N.V., Eindhoven (NL)

(72) Inventors: Franciscus Reinier Antonius Van Der Linde, Schijndel (NL); Marcellinus Petrus Maria Cnoops, Breda (NL); Rudolf Maria Jozef Voncken, Eindhoven (NL); Cornelius Antonius Nicolaas Maria Van Der Vleuten, Liempde (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1133 days.

(21) Appl. No.: 15/505,635

(22) PCT Filed: Sep. 1, 2015

(86) PCT No.: PCT/EP2015/069975
§ 371 (c)(1),
(2) Date: Feb. 22, 2017

(87) PCT Pub. No.: WO2016/034598
PCT Pub. Date: Mar. 10, 2016

(65) Prior Publication Data
US 2017/0273566 A1    Sep. 28, 2017

(30) Foreign Application Priority Data

Sep. 2, 2014    (EP) .................................... 14183221

(51) Int. Cl.
*A61B 5/00*    (2006.01)
*A61B 1/00*    (2006.01)
(Continued)

(52) U.S. Cl.
CPC ........ *A61B 5/0084* (2013.01); *A61B 1/00078* (2013.01); *A61B 1/01* (2013.01);
(Continued)

(58) Field of Classification Search
CPC ........ A61B 2034/2061; A61B 1/00078; A61B 1/0011; A61B 1/01; A61B 34/20;
(Continued)

(56) References Cited

U.S. PATENT DOCUMENTS 5,306,252 A * 4/1994 Yutori ................. A61M 25/005
138/130
5,601,087 A    2/1997 Gunderson et al.
(Continued)

FOREIGN PATENT DOCUMENTS

EP    0397489 A1    11/1990

OTHER PUBLICATIONS

Composite materials guide: Resin Systems—Strength & Stiffness, NetComposites Ltd, Feb. 1, 2001 (Year: 2001).*
(Continued)

*Primary Examiner* — Alexei Bykhovski

(57) ABSTRACT

A guidewire with a cross section of at least a part of its length, comprising a filling material (PLM), a lumen (LM) arranged inside the filling material (PLM) for accommodating an optical fiber (OF) with optical shape sensing properties. One or more stiffening elements (RD) are arranged inside the first material (PLM), wherein the stiffening element(s) (RD) is formed by a material having a higher axial stiffness than the filling material. A braiding structure (BR) encircles all of: the filling material (PLM), the lumen (LM), and the stiffening element(s) (RD). Such guidewire can be designed with a circular symmetric bending behavior, and is thus suitable as an interventional medical device, e.g. for endovascular procedures, and still it can provide optical shape sensing properties.

3 Claims, 7 Drawing Sheets

(51) Int. Cl.
- *A61B 1/01* (2006.01)
- *A61B 34/20* (2016.01)
- *A61M 25/00* (2006.01)
- *A61M 25/09* (2006.01)
- *A61M 25/01* (2006.01)

(52) U.S. Cl.
CPC ............ *A61B 5/6851* (2013.01); *A61B 34/20* (2016.02); *A61M 25/0012* (2013.01); *A61M 25/005* (2013.01); *A61M 25/0053* (2013.01); *A61M 25/09* (2013.01); *A61M 25/09041* (2013.01); *A61B 1/0011* (2013.01); *A61B 2034/2061* (2016.02); *A61M 25/0054* (2013.01); *A61M 2025/0166* (2013.01); *A61M 2025/09108* (2013.01); *A61M 2025/09133* (2013.01)

(58) Field of Classification Search
CPC ..... A61B 5/0084; A61B 5/6851; A61B 1/009; A61M 25/09; A61M 2025/0166; A61M 2025/09108; A61M 2025/09133; A61M 25/0012; A61M 25/005; A61M 25/0053; A61M 25/0054; A61M 25/09041
See application file for complete search history.

(56) References Cited

U.S. PATENT DOCUMENTS

| | | | |
|---|---|---|---|
| 5,810,867 A * | 9/1998 | Zarbatany | A61M 25/0054 604/96.01 |
| 7,527,606 B2 | 5/2009 | Van Oepen | |
| 8,649,847 B1 | 2/2014 | Park et al. | |
| 8,882,705 B2 | 11/2014 | McDaniel et al. | |
| 2001/0021831 A1* | 9/2001 | Fleischhacker | A61M 1/125 604/264 |
| 2002/0005888 A1 | 1/2002 | Obata et al. | |
| 2002/0058888 A1* | 5/2002 | Biagtan | A61M 25/09 600/585 |
| 2002/0115983 A1 | 8/2002 | Sekino et al. | |
| 2004/0082879 A1* | 4/2004 | Klint | A61B 17/12022 600/585 |
| 2007/0005101 A1* | 1/2007 | Fahey | A61F 2/013 606/200 |
| 2007/0191778 A1* | 8/2007 | Venbrux | A61M 25/09 604/164.13 |
| 2008/0194991 A1* | 8/2008 | Teague | B29C 48/154 600/585 |
| 2011/0046607 A1* | 2/2011 | Halevy | A61B 17/00491 604/528 |
| 2011/0098533 A1* | 4/2011 | Onoda | A61B 1/0051 600/117 |
| 2013/0012809 A1 | 1/2013 | Schlesinger et al. | |
| 2013/0158512 A1 | 6/2013 | Gutierrez et al. | |
| 2013/0308138 A1* | 11/2013 | 'T Hooft | G01B 11/18 356/601 |
| 2014/0148673 A1* | 5/2014 | Bogusky | A61M 25/0052 600/374 |
| 2016/0038720 A1* | 2/2016 | Loh | A61M 25/09025 600/585 |
| 2017/0014194 A1 | 1/2017 | Duindam et al. | |

OTHER PUBLICATIONS

Ken Youssefi/Thalia Anagnos, Structures and Stiffness, Introduction to Engineering, Engineering 10, SJSU, slide 33, Oct. 16, 2008 (Year: 2008).*

* cited by examiner

GUIDEWIRE FOR OPTICAL SHAPE SENSING

CROSS-REFERENCE TO PRIOR APPLICATIONS

This application is the U.S. National Phase application under 35 U.S.C. § 371 of International Application Serial No. PCT/EP2015/069975, filed on Sep. 1, 2015, which claims the benefit of European Patent Application No. 14183221.2, filed on Sep. 2, 2014. These applications are hereby incorporated by reference herein.

FIELD OF THE INVENTION

The present invention relates to the field of elongated devices, especially guidewires, more specifically guidewires for optical shape sensing purposes.

BACKGROUND OF THE INVENTION

Optical shape sensing (OSS) can be used to provide navigational guidance for elongated medical devices such as catheters, guidewires, endoscopes, stylets, and needles. To accomplish this, the optical fiber must be an integral part of the medical device. With the integration of the optical fiber in the medical device, the performance of the medical device may not be altered. Since these medical devices are to be used inside the body, e.g. inside narrow blood vessels, they can have only a limited size which consequently limits the space for the optical fiber as well.

With the integration of an OSS fiber, space of an elongated medical device must be sacrificed for the optical fiber to fit in. By removing this space, mechanical properties of the elongated medical device will be lost, and the result is a device with a non-circular bending behavior. Especially, elongated medical devices which are solid are difficult to compensate mechanically when these need to be equipped with a lumen, as it is the case for guidewires that have to be equipped with an OSS fiber.

WO 94/12095 A2 discloses a guidewire which incorporates an optical fiber for diagnozing tissue in vivo. The guidewire comprises a stainless steel thin wall tube. At the distal end of the guidewire, the optical fiber extends through a coil of wire. The guidewire also includes a safety wire extending from the distal end of the tube to the distal end of the coil. The safety wire is formed of stainless steel and brazed to the tube and soldered to the cil. The coil may also be fitted over the distal end of the tube and soldered or brazed in place at solder beads.

US 2002/005888 A1 discloses an elongate member in form of a guidewire, the distal section of which is made at least partially of a fiber composite matrix and has at least one segment with increasing flexibility in a distal direction. In an embodiment, a flexible body is disposed about the distal section of the elongate member, wherein the flexible body can be a helical coil or a polymer layer. The guidewire further has an elongate core disposed in a core lumen of the elongate member. The hollow proximal section of the composite guidewire may be partially or totally filled with a filler material to enhance the attachment strength between the composite guidewire and an extension guidewire. Instead of a filler material, the proximal section of the composite guidewire may have one or several magnets that are incorporated before, during or after the winding process for making the composite guidewire. The magnets serve to attach the extension guidewire to the composite guidewire by magnetic forces.

SUMMARY OF THE INVENTION

Following the above description, it would be advantageous to provide an elongated device, preferably a guidewire, which has a lumen for accommodating an OSS fiber, and which has a circular symmetric or near circular symmetric bending behavior and which is still possible to manufacture with a miniature diameter to allow e.g. interventional medical procedure, e.g. endovascular procedures.

In a first aspect, the invention provides an elongated device with a cross section at least a part of its length, comprising
 a filling material with a first axial stiffness,
 a lumen arranged inside the filling material for accommodating an optical fiber with optical shape sensing properties,
 at least one stiffening element arranged inside the filling material, the at least one stiffening element is formed by a material having a second axial stiffness, and wherein the second axial stiffness is higher than the first axial stiffness, and
 a braiding structure encircling all of: the filling material, the lumen, and the at least one stiffening element.

The invention is based on the insight that it is possible to design an elongated device, especially a guidewire, which has a circular (or substantially circular) bending behavior, in spite of a small cross sectional area and in spite a lumen is included for accommodating an OSS fiber. Preferably, this is combined with the elongated device having a circular or substantially circular cross section. Such elongated device is advantageous e.g. for medical applications as an interventional device, where OSS can be incorporated for navigation purposes without compromising the bending behavior of the elongated device.

Especially, the elongated device may be a guidewire, i.e. it is designed to have the properties with respect to high flexibility, axial stiffness, and a small cross sectional area known for a guidewire, in contrast to a catheter which is thicker and has a lower axial stiffness than a guidewire. A guidewire preferably has an outer diameter of less than 1 mm, such as 0.98 mm or such as 0.89 mm, depending however on its location of use. The structure proposed by the first aspect of the invention is a surprising design for a guidewire, since the structure as defined involves combination of structural elements and manufacturing methods from both traditional guidewires and catheters.

The stiffening element(s) may be formed by a simple structure, e.g. in the form of one or more straight (metal) rods with a circular cross section, e.g. one or more rods formed by a metal which is embedded in the filling material which may be a polymeric. Such polymeric filling material can have a much lower axial stiffness than the one or more stiffening elements which serve to provide the majority of the total axial stiffness of the elongated device. It is to be understood that preferred axial stiffness values depend on the dimensions and transitions over the length of the device.

It is to be understood that the stiffening element inside the filling material is not an essential element for providing a guidewire with an appropriate axial stiffness. The properties of the filling material and the braiding structure may be selected so as to form together an axial stiffness which is sufficient to serve as a guidewire, and still provide a suitable bending property to allow OSS. Thus, the separate stiffening element(s) inside the filling material may be omitted.

In the following, some principal embodiments, and/or additional features to the first aspect, will be defined.

It is preferred that the filling material, the lumen, the stiffening element, and the braiding structure are configured with respect to material stiffnesses, and relative geometrical position, so as to provide a circular or substantially circular bending behavior of at least a length portion of the elongated device. Especially, in case the elongated device is a guidewire, it is preferred that the proximal side of the guidewire has an (almost) circular bending behavior. With the guiding by the detailed embodiments explained later, the skilled person will know how to select suitable materials for the filling material, the stiffening element(s), and the braiding structure, and also be able to propose relative geometrical positions between these elements to obtain a desired bending behavior, in spite the fact that the proposed elongated device combines features known within the technical field of guidewires as well as within the technical field of catheters.

The at least one stiffening element preferably tapers over a length at the distal end portion of the elongated device. The tapering length preferably is at least 250 mm, but may be shorter if needed such as 100 mm, for example. In the proximal portion of the elongated device, the at least one stiffening element preferably has a constant diameter along the length of the proximal portion. For example, the at least one stiffening element has an outer diameter of about 0.10 mm in the proximal portion, and tapers over the tapered length in the distal end portion to about 0.05 mm.

The at least one stiffening element can extend till the distal end of the elongated device or end about maximally 100 mm before the distal end.

The at least one stiffening element is preferably made of stainless steel or Nitinol, but can be any high strength metal and/or alloy like MP35N.

In other embodiments, the at least one stiffening element has a constant outer diameter over its entire length instead of tapering at the distal end. In this case, the at least one stiffening element preferably has an outer diameter of about maximally 0.10 mm throughout the length of the stiffening element.

Especially, the lumen may be arranged in a central portion of the cross section of the elongated device, however, the lumen may alternatively be arranged eccentric to a cross section of the elongated device.

Preferably, the elongated device comprises a plurality of separate stiffening elements arranged inside the filling material, thus obtaining a geometrical distribution of the stiffening effect of the stiffening elements. The plurality of separate stiffening elements may be arranged equally spaced from each other. The plurality of separate stiffening elements may comprise at least two straight stiffening elements. The plurality of separate stiffening elements may comprise two straight rods, e.g. two straight rods having a circular cross sectional area, and e.g. formed by a metal. The plurality of separate stiffening elements may be spiraled around the lumen, e.g. the stiffening elements form respective spirals, seen in an axial direction of the elongated device. Especially, the plurality of separate stiffening elements may comprise two stiffening elements with different cross sectional shape, e.g. a rod with a circular cross section, and a wire with a rectangular cross section. The plurality of separate stiffening elements may be arranged concentric around the lumen, e.g. with the lumen arranged centrally, e.g. with the braiding structure and an overall cross sectional shape of the elongated device being circular, e.g. with the lumen also having a circular cross section.

The filling material may be a polymeric material, and the at least one stiffening element may be formed by a material comprising a metal.

The filling material and a material forming the at least one stiffening material are selected such that the second axial stiffness is at least a factor of 2-100 times higher than the first axial stiffness.

The braiding structure may be formed by a braiding wire structure, e.g. a metal wire, with a pattern such as known within the fields of catheters.

In some embodiments, the braiding structure has a braiding angle which is constant over the entire length of the braiding structure. A preferred braiding angle is about 55°. In general, the braiding angle can be an angle in the range from about 25° to about 70°, if more stiff (small braiding angle) or more flexible (larger braiding angle) guide wires are preferred.

In other embodiments, the braiding angle is not constant over the length of the braiding structure, but is different in the proximal portion of the elongated device than in the distal end portion. This allows for a more optimal distribution of mechanical properties over the length of the device. In particular, the braiding angle is larger in the distal end portion, for example in a range from about 40° to about 60°, than in the proximal portion, where the braiding angle is in a range from about 20° to about 40°.

In connection with an embodiment mentioned above, according to which the at least one stiffening element ends in a certain distance, for example about 100 mm, proximal of the distal end, the braiding structure preferably extends till the distal end, i.e. extends beyond the distal end of the at least one stiffening element. Vice versa, in connection with an embodiment mentioned above, according to which the at least one stiffening element extends till the distal end of the elongated device, the braiding structure preferably ends about maximally 100 mm before the distal end of the elongated device, i.e. ends before the distal end of the stiffening element.

The braiding wires forming the braiding structure can have any cross-sectional geometries, while rectangular or circular cross-sections are preferred. The cross-sectional dimensions of the braiding wires preferably are about 25× about 125 microns when being rectangular and about 50 microns in diameter when being circular.

Further, the braiding structure preferably has a tubular shape with a constant outer diameter over its length. However, in particular in connection with an embodiment mentioned above, according to which the at least one stiffening element has a tapering distal end portion, the braiding structure preferably tapers in its distal end portion. In particular, the tapering profile of the braiding structure preferably follows the tapering profile of the at least one stiffening element in this case.

The elongated device may comprise a cover or "jacket" for covering the braiding structure, such as a cover or "jacket" formed by a polymeric material.

The lumen is understood to be a space, e.g. a hole, large enough to allow an OSS fiber to be arranged therein during bending, in order to be able to track the shape of the elongated device during bending.

The elongated device may comprise an optical fiber (OSS fiber) with optical shape sensing properties arranged inside the lumen, wherein the proximal end of the elongated device is arranged to allow connection of the proximal end of the OSS fiber to an optical console for optical interrogation of the OSS fiber. The OSS fiber may comprise wavelength dependent deflecting structures to allow optical shape sensing properties along at least a part of its longitudinal extension, such as Bragg gratings, so as to allow optical shape sensing (OSS) of at least a longitudinal part of the elongated device. This allows a user, e.g. medical personnel, to effectively navigate when being able to steer the elongated device and preferably in real time see the actual shape of the elongated device visually reconstructed by means of OSS interrogation. The OSS fiber may especially have backscattering properties comprising at least one of: Rayleigh scattering and fiber Bragg gratings. The OSS fiber may be a multicore optical fiber comprising a plurality of fiber cores, such as comprising 1-10 fiber cores, e.g. 4 or 7 fiber cores. One or more additional fibers to be accommodated within the lumen of the elongated device may be provided so as to allow one or more of: spectroscopy, delivery of optical power, illumination, endoscopy, and data transfer, in addition to OSS.

In a special application, the elongated device is an interventional medical device, such as a medical guidewire or a medical catheter, or a guidewire arranged for insertion into a medical catheter. Such medical device may comprise a medical functionality, e.g. endoscopy, spectroscopy, application of heat, ablation etc.

In a second aspect, the invention provides an optical shape sensing system comprising
  an elongated device, e.g. a guidewire, according to the first aspect,
  an optical fiber with optical shape sensing properties along at least a part of its length, wherein the optical fiber is arranged for insertion into the lumen of the elongated device so as to follow a shape of the elongated device, and
  an optical console system arranged for interrogating said optical shape sensing properties of the optical fiber, and to accordingly determine a measure of a three-dimensional shape of at least a part of the elongated device.

Especially, the system may comprise a display arranged to visualize said three-dimensional shape.

In a third aspect, the invention provides a method of manufacturing an elongated device, the method comprising
  providing an elongated structure by a filling material formed by a material having a first stiffness,
  providing at least one stiffening element formed by a material having a second stiffness, and wherein the second stiffness is higher than the first stiffness,
  providing a braiding structure,
  forming a lumen inside the elongated structure formed by the filling material,
  arranging the at least one stiffening element inside the elongated structure, and
  encircling all of: the elongated structure, the lumen, and the at least one stiffening element by the braiding structure.

Especially, the method is a method of manufacturing a guidewire, e.g. a guidewire suitable as a medical interventional device.

It is appreciated that the same advantages and embodiments of the first aspect apply as well for the second and third aspects. In general the first, second and third aspects may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DETAILED DESCRIPTION OF EMBODIMENTS

Figure 1:
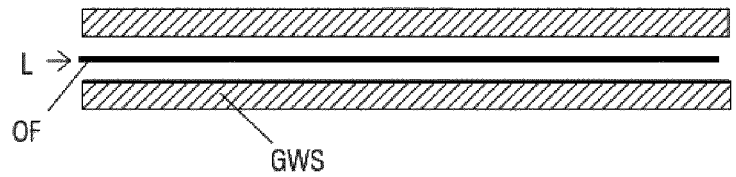
FIG. 1 shows the guidewire with an OSS fiber arranged in a lumen.

FIG. 1 shows a longitudinal section sketch of an elongated device embodiment in the form of a guidewire. A flexible guidewire structure GWS, to be explained in further details later, has a lumen shaped to provide space for an OSS fiber OF to which light L can be applied for optical interrogation, and OSS to allow reconstruction of the shape if the guidewire.

Figure 2:
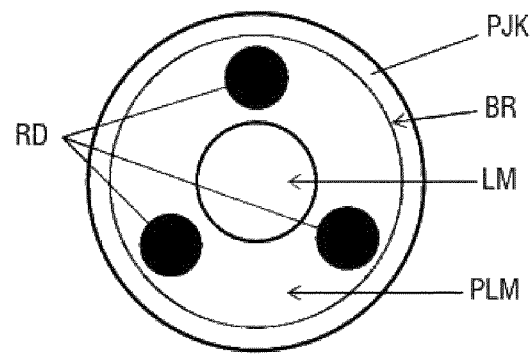
FIG. 2 illustrates an cross sectional sketch of an embodiment.

FIG. 2 shows a cross sectional sketch of an embodiment in the form of a guidewire. Here, the lumen LM for the OSS fiber is positioned in the center of the guidewire which has an overall circular cross sectional shape. Three rods RD, here shown with circular cross section, are equally spaced from each other. The rods RD serve as stiffening elements and are cast or embedded within a polymeric filling material PLM. A braiding structure BR encircles the cross sectional area which includes the lumen LM, the rods RD and the filling material PLM, i.e. over the entire circumference. A polymer "jacket" PJK serves to cover the braiding structure BR.

The three stiffening rods RD can be made from any metal or other stiff material, i.e. with an axial stiffness which is higher than the stiffness of the filling material PLM, and will ensure (almost) circular symmetry in bending while providing additional axial stiffness.

With the braiding structure BR, a torque from proximal to distal of the guidewire can transferred. The braiding wire forming the braiding structure BR can be made of different materials and can have the form of a wire like stainless steel, copper, Kevlar, nylon, or any other type of metal or polymer. In a variant, it is to be understood that even more than three (identical or different) rods can be distributed in the filling material PLM, e.g. 4, 5, 6, or even more separate stiffening elements.

Figure 3A:
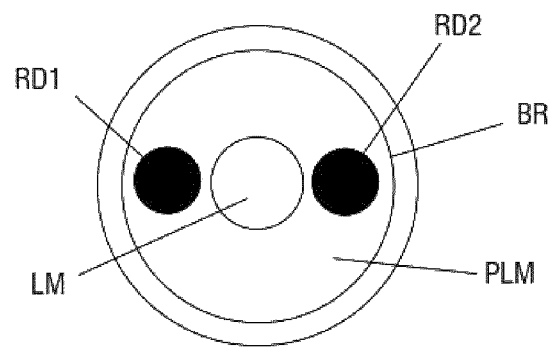
FIGS. 3a and 3b illustrates a cross sectional sketch and a longitudinal section of another embodiment, respectively.
Figure 3B:
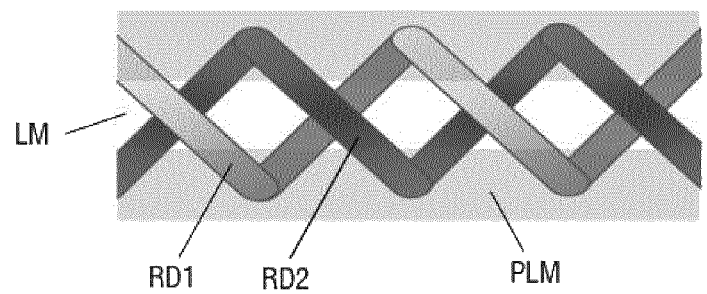

FIG. 3*a* shows a cross sectional sketch, and FIG. 3*b* shows a longitudinal view another guidewire embodiment, which however has the same braiding structure BR, and filling material PLM, and has an overall circular cross section, as in FIG. 2. Here, two stiffening rods RD1, RD2 are counter spiraled around the lumen LM to ensure almost circular symmetry in bending, while providing additional axial stiffness. The counter spiraled stiffening rods RD1, RD2 arranged within the filling material PLM are shown in FIG. 3*b*. In an example, the stiffening rods RD1, RD2 are spiraled to provide at least 1 spiral revolutions per meter, but can have more spiral revolutions per meter to increase the flexibility and torque response of the guide wire.

Figure 4:
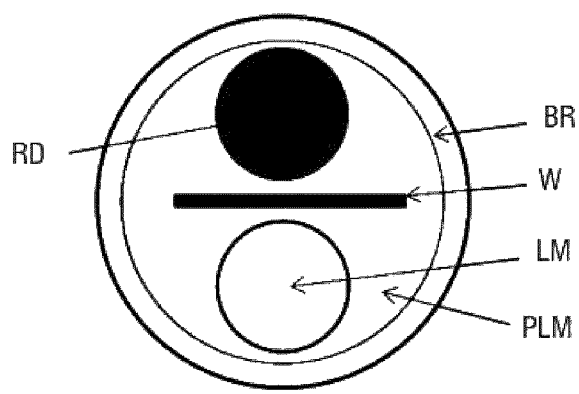
FIG. 4 illustrates a cross sectional view of yet another embodiment.

FIG. 4 shows a cross sectional sketch of still another guidewire embodiment which has a similar braiding structure BR, and filling material PLM, and has an overall circular cross section, as in FIG. 2. In FIG. 4, the OSS lumen LM is placed eccentric with a stiffening RD rod with circular cross section, and an additional stiffening element in the form of a wire W with a rectangular cross sectional shape. The rod RD and rectangular wire W will provide axial and bending stiffness where the bending stiffness can be made equal for both main bending directions by a well-chosen design. The braiding structure BR is placed around over the entire circumference, covered e.g. by a polymer "jacket". The rod RD and/or wire W can be made of any metal or other stiff material.

The shown elongated device embodiments are in the form of guidewires, since it is appreciated that it is possible to provide OSS fiber properties within a thin guidewire to allow medical applications in the form of e.g. endovascular procedures, and still maintain a high flexibility in combination with a high axial stiffness. However, the structural design may be considered to resemble a microcatheter.

Figure 5A:
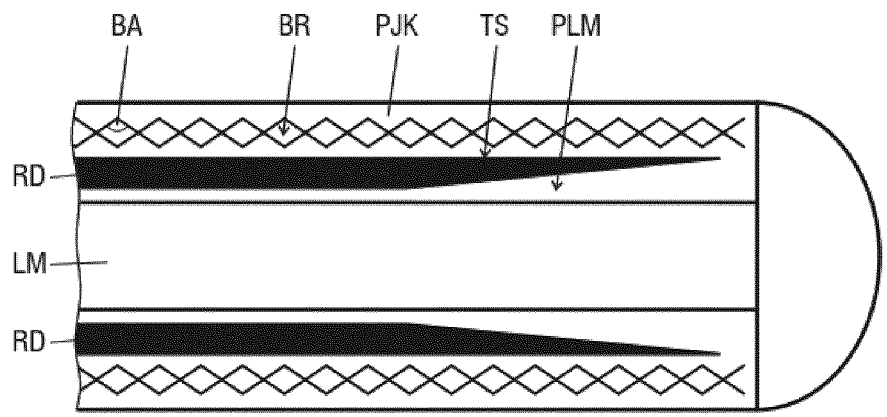
FIG. 5a illustrates a longitudinal section of a distal end portion of a guidewire of another embodiment.
Figure 5B:
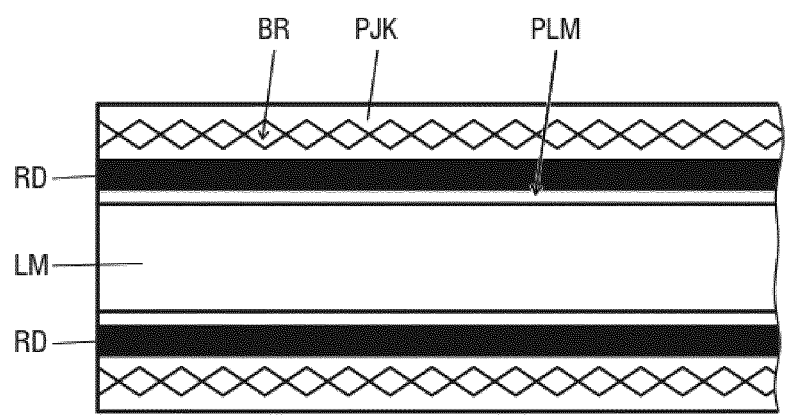
FIG. 5b illustrates a longitudinal section of a proximal portion of the guide wire of the embodiment in FIG. 5a,
  FIG. 6a illustrates a longitudinal section of a distal end portion of a guidewire of another embodiment.

FIG. 5*a* shows a longitudinal sectional sketch of a distal end portion of still another guidewire embodiment. FIG. 5*b* shows a longitudinal sectional sketch of a proximal portion of the embodiment in FIG. 5*a*. In cross-section, the embodiment in FIGS. 5*a* and 5*b* is similar with the embodiment in FIG. 2, i.e. has a central lumen LM, three stiffening elements RD placed 120° from each other about the longitudinal axis, and a filling material PLM in which the stiffening elements RD are embedded. A brading structure BR is placed around over the entire circumference with respect to the longitudinal axis of the device. A polymer "jacket" PJK covers the arrangement.

In this embodiment, the stiffening elements RD extend over the entire length of the guidewire or end proximal of the distal end, in this case preferably maximally about 100 mm proximal of the distal end.

According to FIG. 5*b*, the stiffening elements RD which are configured as wires or rods, have a constant diameter in the proximal portion of the guidewire. In the distal end portion shown in FIG. 5*a*, the stiffening elements RD have a tapering section TS, in which the stiffening elements RD taper over a length of preferably at least 250 mm, or less if needed.

In a preferred example, the outer diameters of the stiffening elements RD are about 0.10 mm in the proximal portion according to FIG. 5*b*, while the outer diameters of the stiffening elements RD taper in the tapering section TS from 0.10 mm to about 0.05 mm. The stiffening elements RD are preferably made of stainless steel or nitinol, but can be any high strength metal and/or alloy like MP35N. The braiding structure BR has a braiding angle BA which is constant over the entire length of the braiding structure BR. The braiding structure BR extends til the distal end of the guidewire in a configuration where the stiffening elements RD end proximal of the distal end. Vice versa, in case the stiffening elements RD end at the distal end of the guidewire, the braiding structure BR ends about maximally 100 mm proximal of the distal end.

The braiding angle BA is in a range from about 25° to about 70°. The lower the braiding angle is, the stiffer is the braiding structure BR and, thus, the guidewire, while larger braiding angles BA lead to more flexible guidewires. In a preferred example, the braiding angle BA is about 55°.

The braiding structure BA is formed by braiding wires which are rectangular or circular in cross-section. In a preferred example, the braiding wires have a cross-sectional size of 25×125 micron when being rectangular, or 50 micron in diameter when being circular in cross-section.

In the embodiment shown, the maximum outer diameter of the total guidewire is about 0.98 mm, but can also be thinner, such as about 0.89 mm.

Figure 6A:
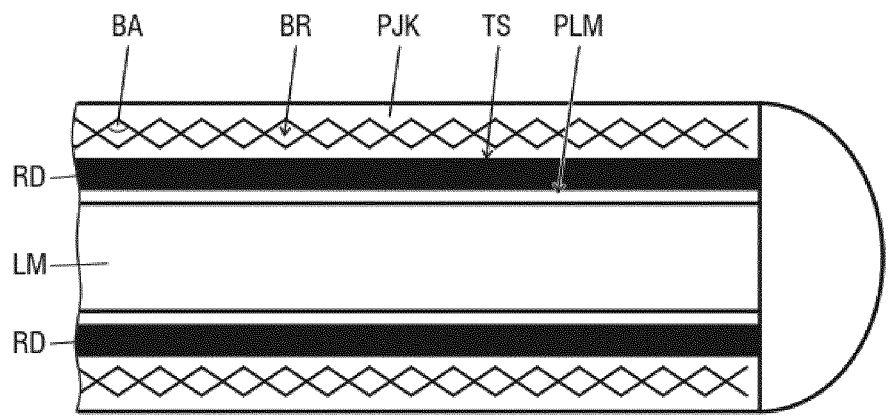
FIG. 6b illustrates a longitudinal section of a proximal portion of the guide wire of the embodiment in FIG. 6a,
  FIG. 7a illustrates a longitudinal section of a distal end portion of a guidewire of another embodiment.
Figure 6B:
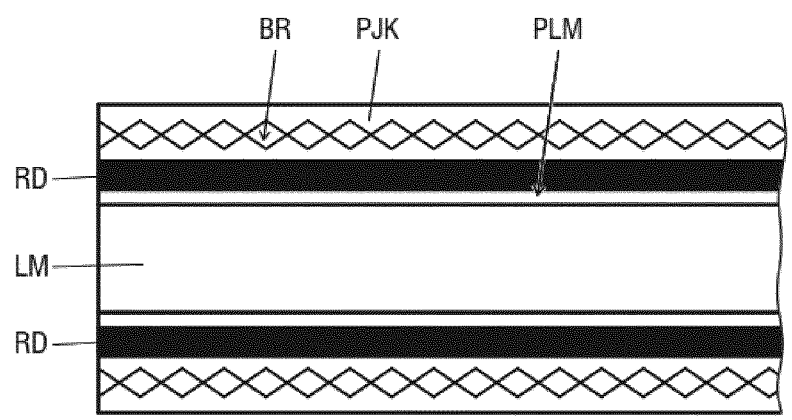

FIG. 6*a* shows a longitudinal sectional sketch of a distal end portion of still another embodiment of a guidewire, and FIG. 6*b* shows a longitudinal sectional sketch of a proximal portion of the same guidewire. This embodiment is similar to the embodiment shown in FIGS. 5*a* and 5*b* with the difference that the stiffening elements RD are straight over their entire length, i.e. do not taper in the distal end portion of the device.

In a preferred example, the outer diameter of the stiffening elements RD is constant and about maximally 0.10 mm, and can be smaller if preferred.

Figure 7A:
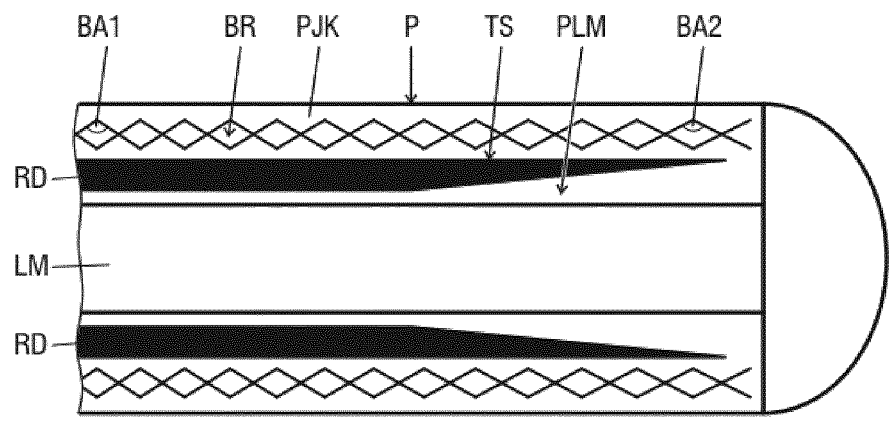
FIG. 7b illustrates a longitudinal section of a proximal portion of the guide wire of the embodiment in FIG. 7a,
  FIG. 8a illustrates a longitudinal section of a distal end portion of a guidewire of another embodiment.
Figure 7B:
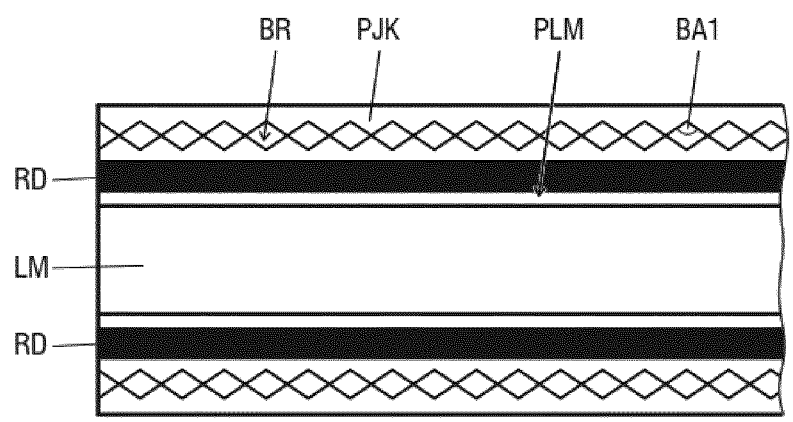

FIG. 7*a* shows a longitudinal sectional sketch of a distal end portion of a guidewire according to a further embodiment, and FIG. 7*b* shows a longitudinal sectional sketch of the proximal portion of this guidewire.

This embodiment is similar to the embodiment shown in FIGS. 5*a* and 5*b*, with the difference that the braiding angle of the braiding structure BR is different in the proximal portion of the guidewire (FIG. 7*b*) than in the distal end portion of the guidewire (FIG. 7*a*). In particular, the braiding structure BR has a first braiding angle BA1 in the proximal portion, and a second braiding angle BA2 in the distal end portion of the guidewire. The braiding structure BR can be made such that there is a continuous transition from the braiding angle BA1 to the second braiding angle BA2 along the length of the braiding structure BR, or there is a position P along the length of the braiding structure BR at which the braiding angle discontinuously changes from the braiding angle BA1 to the braiding angle BA2. The position P can coincide with the proximal end of the tapering sections TS of the stiffening elements RD.

In particular, the braiding angle BA2 is larger than the braiding angle BA1. In a preferred example, the braiding angle BA1 is in a range from about 20° to about 40°, while the braiding angle BA2 is in a range from about 40° to about 60°.

A varying braiding angle over the length of the braiding structure and, thus, the guidewire, allows for a more optimal distribution of mechanical properties over the length of the braiding structure and, thus, the guidewire.

Figure 8A:
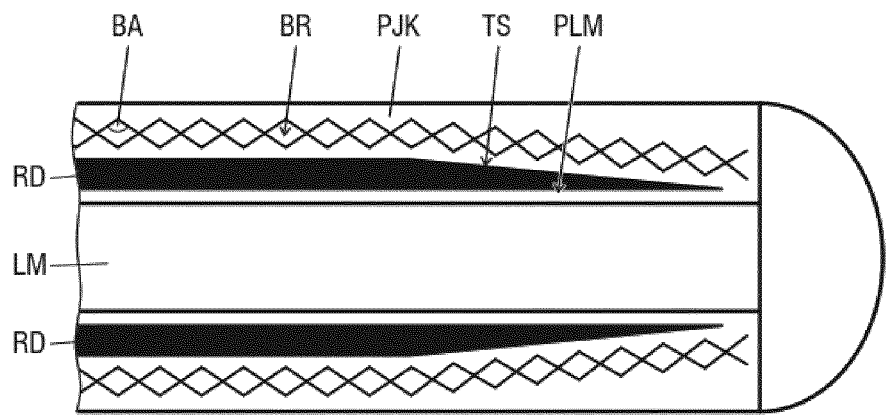
FIG. 8b illustrates a longitudinal section of a proximal portion of the guide wire of the embodiment in FIG. 8a,
  FIG. 9 illustrates basic parts of a system embodiment.
Figure 8B:
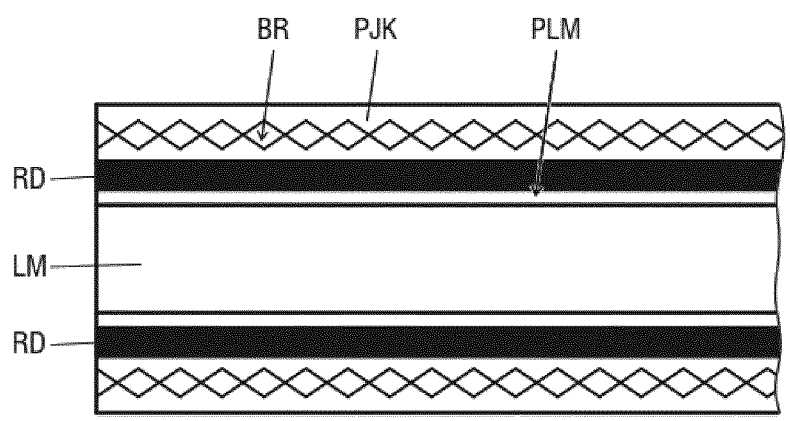

FIG. 8*a* shows a longitudinal sectional sketch of a distal end portion of a guidewire according to a further embodiment, and FIG. 8*b* shows a longitudinal section sketch of a proximal portion of this guidewire.

This embodiment is similar to the embodiment shown in FIGS. 5*a* and 5*b* with the difference that the braiding structure BR tapers in the distal end portion of the guidewire. This means, since the braiding structure BR has a tubular shape, that the outer diameter of the braiding structure BR decreases towards the distal end in the distal end portion of the guidewire. In particular, the tapering profile of the braiding structure BR can follow the tapering profile of the stiffening elements RD. Such a configuration increases the flexibility of the guidewire at the distal end thereof.

It is to be understood that features of the embodiments according to FIGS. 5a, 5b to 8a, 8b can be combined with one another. For example, in the embodiment according to FIGS. 8a and 8b, the braiding structure BR can have a varying braiding angle between the proximal portion and the distal end portion as described with respect to FIGS. 7a and 7b. Other combinations are also conceivable to a person skilled in the art.

Figure 9:
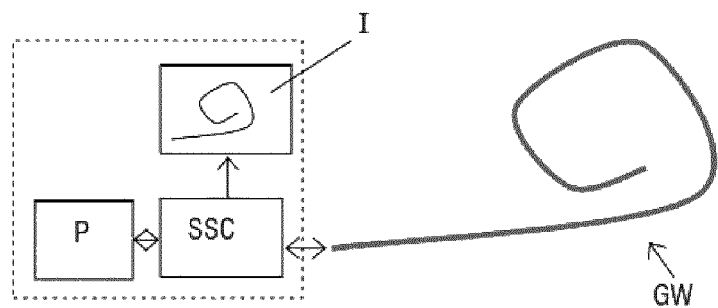

FIG. 9 illustrates basic parts of a system embodiment where a medical guidewire GW according to the invention, which has an OSS fiber arranged inside. A processor P is arranged to control an optical shape sensing console SSC which is connected to the OSS fiber arranged inside the guidewire GW, and arranged to optically interrogate strain sensing optical elements in the OSS fiber. Accordingly, an image I of a three-dimensional shape of at least a part of the OSS fiber can be reconstructed, and thereby also of a three-dimensional shape of at least a part of the guidewire GW, and thus also a catheter in which the guidewire GW may be inserted. E.g. such 3D image I can be displayed as an image I on a monitor in real time.

Especially, the system may form part of an interventional medical examination system which allows the user to navigate an interventional medical instrument inside during an interventional procedure.

Figure 10:
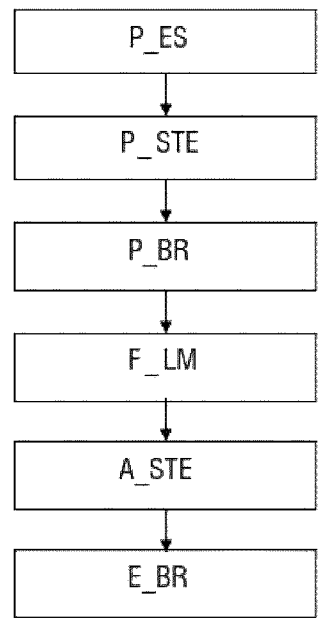
FIG. 10 shows steps of a method embodiment.

FIG. 10 shows steps of an embodiment of a method of manufacturing a guidewire. The method comprises providing P_ES an elongated structure by a filling material formed by a material having a first axial stiffness, providing P_STE at least one stiffening element formed by a material having a second stiffness, and wherein the second stiffness is higher than the first stiffness, and providing P_BR a braiding structure. A lumen is formed F_LM inside the elongated structure formed by the first material, and the at least one stiffening element is arranged A_STE inside the elongated structure, such as cast or in other ways embedded therein. The braiding structure is then encircled E_BR around all of: the elongated structure, the lumen, and the at least one stiffening element. Further, the method may comprise the step of arranging an OSS fiber inside the lumen.

It is to be understood, that the steps may be performed in a different order than mentioned above, such as known by the person skilled within manufacturing of guidewires and/or catheters.

To sum up the invention provides a guidewire with a cross section of at least a part of its length, comprising a filling material PLM, a lumen LM arranged inside the filling material PLM for accommodating an optical fiber OF with optical shape sensing properties. One or more stiffening elements RD are arranged inside the first material PLM, wherein the stiffening element(s) RD is formed by a material having a higher axial stiffness than the filling material. A braiding structure BR encircles all of: the filling material PLM, the lumen LM, and the stiffening element(s) RD. Such guidewire can be designed with a circular symmetric bending behavior, and is thus suitable as an interventional medical device, e.g. for endovascular procedures, and still it can provide optical shape sensing properties.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An elongated device, comprising:
a cross section over at least part of the elongated device, the cross section including:
a filling material with a first axial stiffness;
a lumen arranged inside the filling material, wherein the lumen is configured to accommodate an optical fiber with optical shape sensing properties;
at least one stiffening element arranged inside the filling material and outside the lumen,
wherein the at least one stiffening element is formed by a material having a second axial stiffness, and wherein the second axial stiffness is higher than the first axial stiffness; and
a braiding structure encircling all of: the filling material, the lumen, and the at least one stiffening element, wherein the filling material, the lumen, the at least one stiffening element, and the braiding structure are configured with respect to material stiffnesses, and relative geometrical position, so as to provide a circular or substantially circular bending behavior of at least a length portion of the elongated device;
wherein the at least one stiffening element includes a plurality of separate stiffening elements arranged inside the filling material; and
wherein said plurality of separate stiffening elements are spiraled around the lumen.

2. An elongated device, comprising:
a cross section over at least part of the elongated device, the cross section including:
a filling material with a first axial stiffness;
a lumen arranged inside the filling material, wherein the lumen is configured to accommodate an optical fiber with optical shape sensing properties;
at least one stiffening element arranged inside the filling material and outside the lumen,
wherein the at least one stiffening element is formed by a material having a second axial stiffness, and wherein the second axial stiffness is higher than the first axial stiffness; and
a braiding structure encircling all of: the filling material, the lumen, and the at least one stiffening element, wherein the filling material, the lumen, the at least one stiffening element, and the braiding structure are configured with respect to material stiffnesses, and relative geometrical position, so as to provide a circular or substantially circular bending behavior of at least a length portion of the elongated device; and further comprising:

a wire arranged inside the filling material and outside the lumen, wherein the wire and one stiffening element or each stiffening element of the at least one stiffening element have different cross sectional shapes.

3. An elongated device, comprising a cross section over at least part of the elongated device, the cross section including:

a filling material with a first axial stiffness;

a lumen arranged inside the filling material, wherein the lumen is configured to accommodate an optical fiber with optical shape sensing properties;

at least one rod arranged inside the filling material and outside the lumen, wherein the at least one rod is formed by a material having a second axial stiffness, and wherein the second axial stiffness is higher than the first axial stiffness; and a braiding structure encircling all of: the filling material, the lumen, and the at least one rod, wherein the at least one rod provides axial stiffness, which is higher than the first axial stiffness of the filling material, resulting in a circular or substantially circular bending behavior of at least a length portion of the elongated device; and further comprising:

a wire arranged inside the filling material and outside the lumen, wherein the wire and one rod or each rod of the at least one rod have different cross sectional shapes.

\* \* \* \* \*